(12) United States Patent
Gomez et al.

(10) Patent No.: US 11,844,896 B2
(45) Date of Patent: Dec. 19, 2023

(54) BALANCED ERGONOMIC SURGICAL HANDLE

(71) Applicant: Innerspace Surgical Corporation, Coconut Creek, FL (US)

(72) Inventors: Ricardo Alexander Gomez, Lighthouse, FL (US); Sandy Lawrence Heck, Los Angeles, CA (US); Eric William Conley, South Berwick, ME (US)

(73) Assignee: New Wave Endo-Surgical Corp., Coconut Creek, FL (US)

( * ) Notice: Subject to any disclaimer, the term of this patent is extended or adjusted under 35 U.S.C. 154(b) by 1187 days.

(21) Appl. No.: 16/293,887

(22) Filed: Mar. 6, 2019

(65) Prior Publication Data

US 2019/0274666 A1   Sep. 12, 2019

Related U.S. Application Data

(60) Provisional application No. 62/639,081, filed on Mar. 6, 2018.

(51) Int. Cl.

| | |
|---|---|
| *A61M 1/00* | (2006.01) |
| *A61B 18/14* | (2006.01) |
| *A61B 17/00* | (2006.01) |
| *A61B 18/00* | (2006.01) |
| *A61B 90/92* | (2016.01) |

(52) U.S. Cl.
CPC ........... *A61M 1/85* (2021.05); *A61B 18/1482* (2013.01); *A61M 1/774* (2021.05); *A61B 90/92* (2016.02); *A61B 2017/00292* (2013.01); *A61B 2017/00424* (2013.01); *A61B 2018/00101* (2013.01); *A61B 2018/00577* (2013.01); *A61B 2218/002* (2013.01); *A61B 2218/007* (2013.01)

(58) Field of Classification Search
None
See application file for complete search history.

(56) References Cited

U.S. PATENT DOCUMENTS

| | | | |
|---|---|---|---|
| 6,352,539 B1 * | 3/2002 | Avellanet | A61F 2/86 606/113 |
| 10,314,638 B2 * | 6/2019 | Gee | A61B 18/085 |
| 2006/0025749 A1 * | 2/2006 | Moenning | A61M 25/0662 604/161 |
| 2007/0135812 A1 * | 6/2007 | Sartor | A61B 18/1482 606/49 |
| 2010/0004677 A1 * | 1/2010 | Brostoff | A61B 17/2909 606/205 |
| 2016/0135872 A1 * | 5/2016 | Minnelli | A61B 17/320016 606/34 |
| 2019/0125385 A1 * | 5/2019 | Scheib | A61B 17/29 |
| 2019/0343578 A1 * | 11/2019 | Olson | A61B 18/1492 |
| 2021/0402076 A1 * | 12/2021 | Lee | A61M 1/772 |

\* cited by examiner

*Primary Examiner* — Joanne M Rodden
*Assistant Examiner* — Nora W Rhodes
(74) *Attorney, Agent, or Firm* — Grogan, Tuccillo & Vanderleeden, LLP (57) ABSTRACT

An ergonomic medical device handle which allows for multiple type grip styles and reduces operator fatigue by balancing the weight of the device about a fulcrum point. More particularly a laparoscopic suction irrigation device having its tubing centrally located to allow the handle to rest comfortably and balanced on the hand in any of the commonly used grips. This dramatically reduces the fatigue associated with holding devices for long periods of time.

19 Claims, 6 Drawing Sheets

PISTOL GRIP

FIG. 4A

FLUTE GRIP

FIG. 4B

REMOTE GRIP

FIG. 5A

CAMERA GRIP

FIG. 5B

Pencil Grip

FIG. 6

BALANCED ERGONOMIC SURGICAL HANDLE

CROSS-REFERENCE TO RELATED APPLICATIONS

This application claims the priority benefit of U.S. Provisional Patent Application No. 62/639,081 filed on Mar. 6, 2018, entitled "Balanced Ergonomic Surgical Handle" of Ricardo Alexander Gomez, Sandy Lawrence Heck, Eric William Conley, hereby incorporated by reference for all that is disclosed as though fully set forth herein.

FIELD OF THE INVENTION

The present invention relates to surgical instruments and, more specifically, to a balanced, weighted suction irrigator device used in laparoscopic surgery having an ergonomic handle. The balanced ergonomic surgical handle is designed to minimizing fatigue to the user and to accommodate multiple grip styles.

BACKGROUND OF THE INVENTION

The use of medical instruments is a necessity in modern surgery. Many of the surgical procedures performed today are laparoscopic in nature. Laparoscopy, which is a form of endoscopy, is performed in the abdomen of a patient through small holes made in the abdominal wall. Due to the small ports used, specialized tools are required.

Studies have shown that as laparoscopic techniques develop, greater demands are placed on surgeons. Poorly designed laparoscopic tools increase physician fatigue, particularly of the hands. Accordingly, there will always be a need for well designed handles especially as advances in technology continue. A good understanding of handle designs is important for many reasons. In surgical procedures, it is important to consider the efficiency, safety, and accommodation to the intended user. Is the user sitting down, standing or moving? Determination must also be taken as to whether the handles need to be small, large, soft, stiff, sharp or extra safe. In addition, when dealing with robotics, special consideration must to be taken to help plan a good working relation. The interface between the desired result and the hand of the user is a considerable factor. A handle that is not accommodating can result in unnecessary fatigue and may be inefficient to use.

Suction/irrigator devices are one type of instrument used in laparoscopic surgeries, and have an elongated shaft that is adapted to pass through the lumen of a trocar, and long tubes attached to them that are used for administering or removing fluids encountered during surgery. The tubes are typically adjoined and located at the proximal end of the device. Surgical procedures may take hours to perform, and often require a person to hold the instrument in place. The longer the procedure the longer the fatigue caused on the hands.

Existing suction/irrigator devices typically use rigid elongated shafts that are inserted through a trocar and adapted to be coupled to a suction/irrigation source used for flushing liquid such as saline inside the abdomen. Its main purpose is to irrigate or evacuate bodily fluids from an abdominal area. The knobs that activate the action are usually spring loaded to a valve. The device is commonly held throughout the procedure; when the knobs are depressed by the finger actions, they provide a suction or irrigation action. Most such devices are designed to be used like a trumpet, or pistol, with the problem being that the connected tubing pulls the handle in different directions, particularly upwardly. Accordingly, during surgical procedures surgeons counter-balance the upward motion of such devices by pushing down with force, which can cause fatigue over the course of the procedure.

Further to the above, depending on the type of instrument and on the surgeon's personal preference, different grip styles can be needed, requiring that current instruments be offered with different handles to accommodate different grips such as, for example, "Pistol Grip", "Flute Grip", "Remote Grip", "Camera Grip" and "Pencil Grip". This is costly and burdensome for hospitals, since they must stock multiple versions of each instrument and keep track of which surgeon needs which type of handle.

In view of the above, there is a need for an ergonomic surgical handle that minimizes operator fatigue and accommodates or provides for a variety of different grip positions.

SUMMARY OF THE INVENTION

It is an object of the present invention to provide an ergonomically balanced handle that can be used in laparoscopic surgery.

A further object of the invention is to provide a lightweight handle that reduces the fatigue on the hands of the holder, caused by the weight of the suction/irrigation tubing pulling on the device.

A further object of the invention is to provide a handle shape that allows the user to grip the handle in several of the different methods/styles commonly used during laparoscopy, including, but not limited to, the "Pistol Grip", "Flute Grip", "Remote Grip", "Camera Grip" and "Pencil Grip".

A further object of the invention is to provide an ergonomic handle having a "universal" handle shape that accommodates all of the most common types of grips, and which has buttons positioned in a way that allows the fingers to access them in all the different grip positions. The tubing is positioned in a way that allows it to be incorporated into the grip, rather than interfere with it. The handle also has a space for the purlicue of the hand to fit, so that the handle can rest comfortably and securely in the hand.

The present invention overcomes the deficiencies of the known art and the problems that remain unsolved by providing an ergonomically balanced medical device that fits comfortably in the user's hand and reduces the fatigue associated with prolonged use in this unbalanced position over an extended period of time. These and other aspects, features, and advantages of the present invention will become more readily apparent from the attached drawings and the detailed description of the preferred embodiments, which follow.

BRIEF DESCRIPTION OF THE DRAWINGS

The preferred embodiments of the invention will hereinafter be described in conjunction with the appended drawings provided to illustrate and not to limit the invention, in which.

Like reference numerals refer to like parts throughout the several views of the drawings.

DETAILED DESCRIPTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Figure 1:
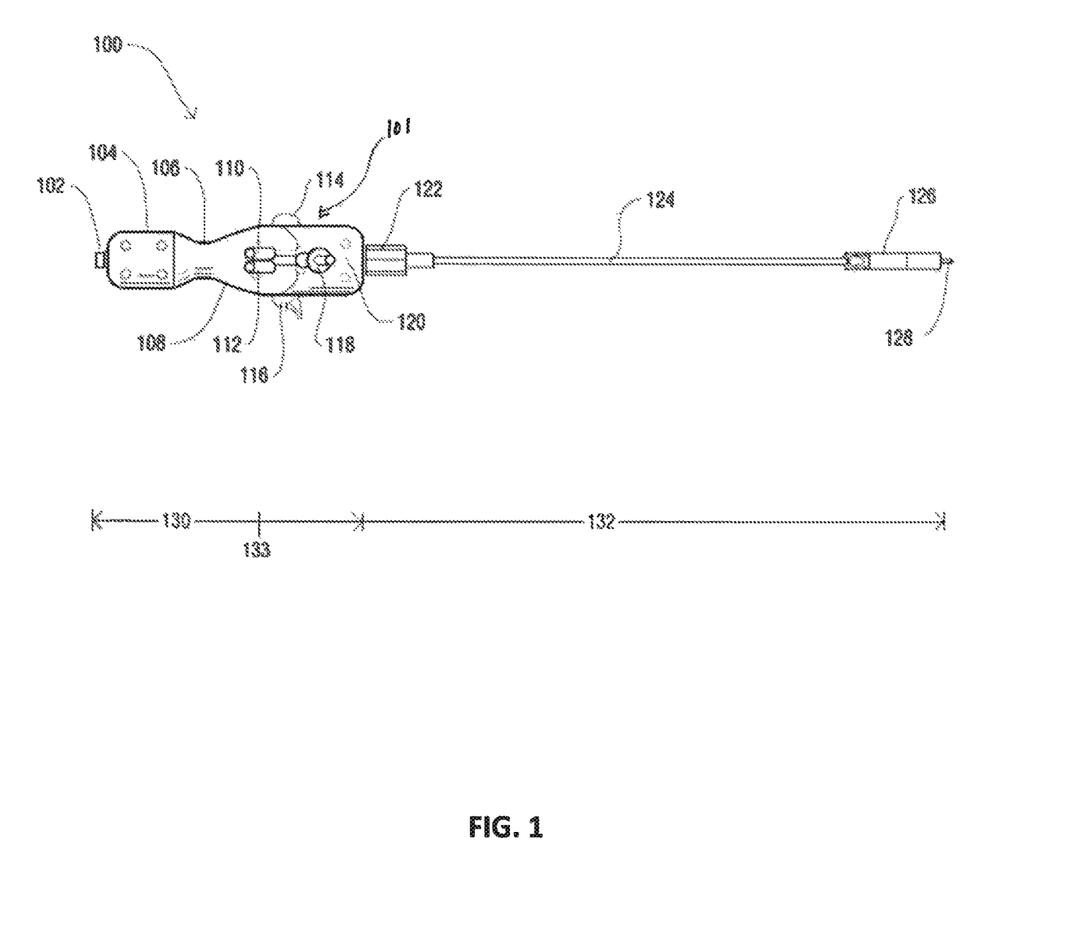
FIG. 1 presents a bottom perspective view of an exemplary suction/irrigation device.
Figure 2:
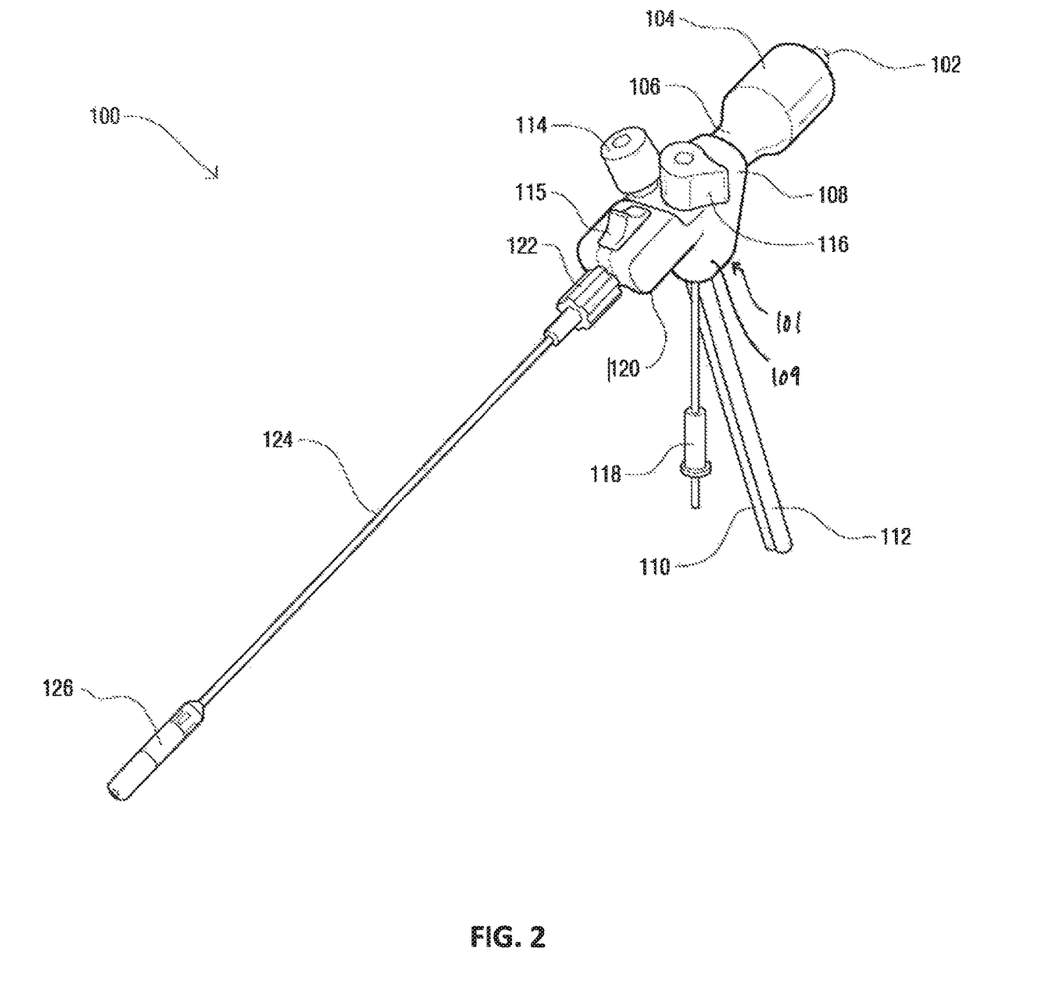
FIG. 2 presents a top left side, perspective view of the exemplary suction irrigator device.
Figure 3:
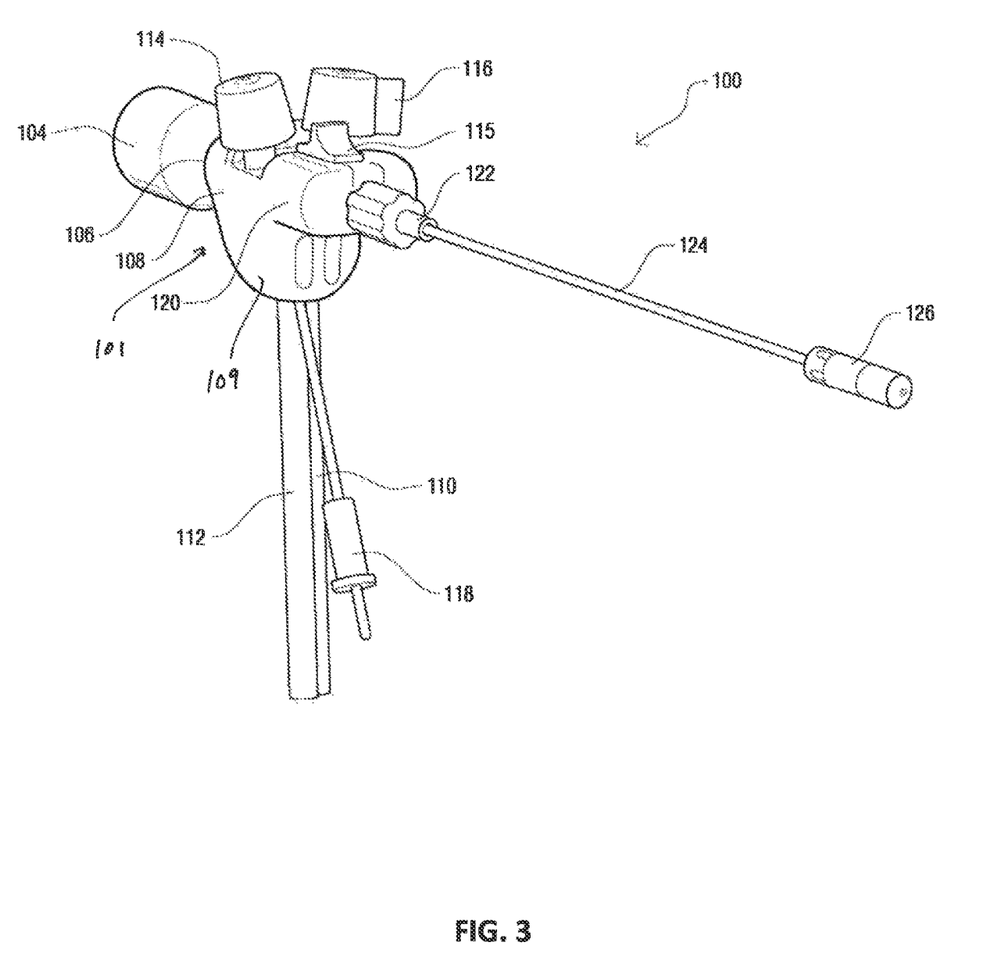
FIG. 3 presents a side perspective view of the exemplary suction irrigator device.
Figure 4A:
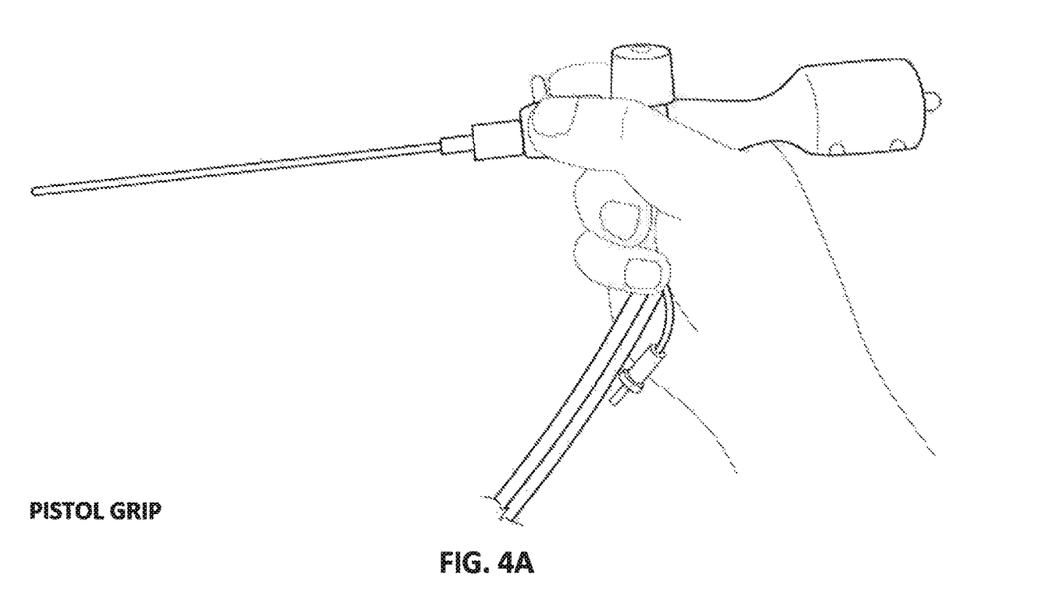
FIG. 4A presents a perspective view of the Pistol Grip.
Figure 4B:
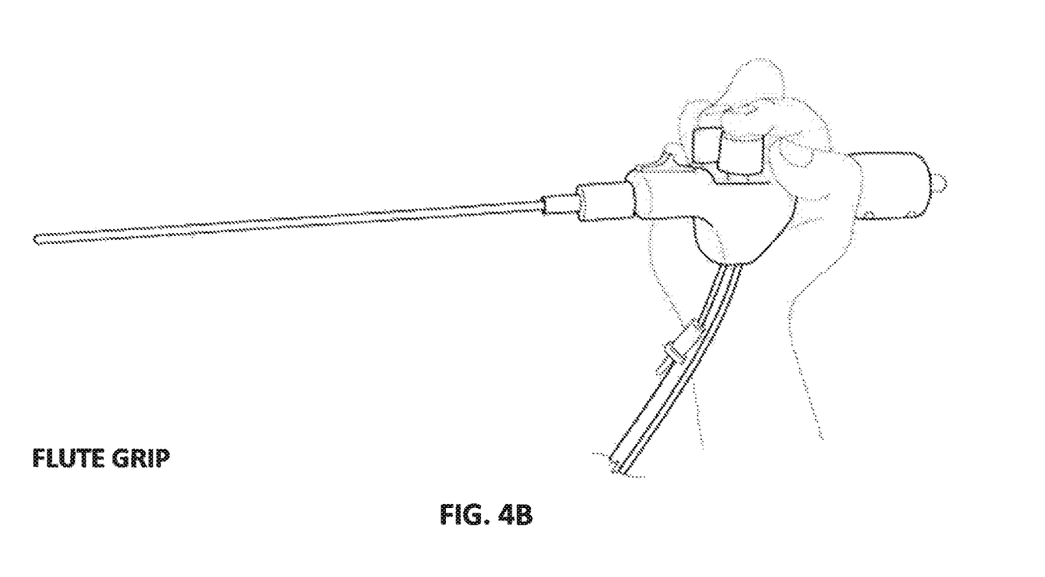
FIG. 4B presents a perspective view of the Flute Grip.
Figure 5A:
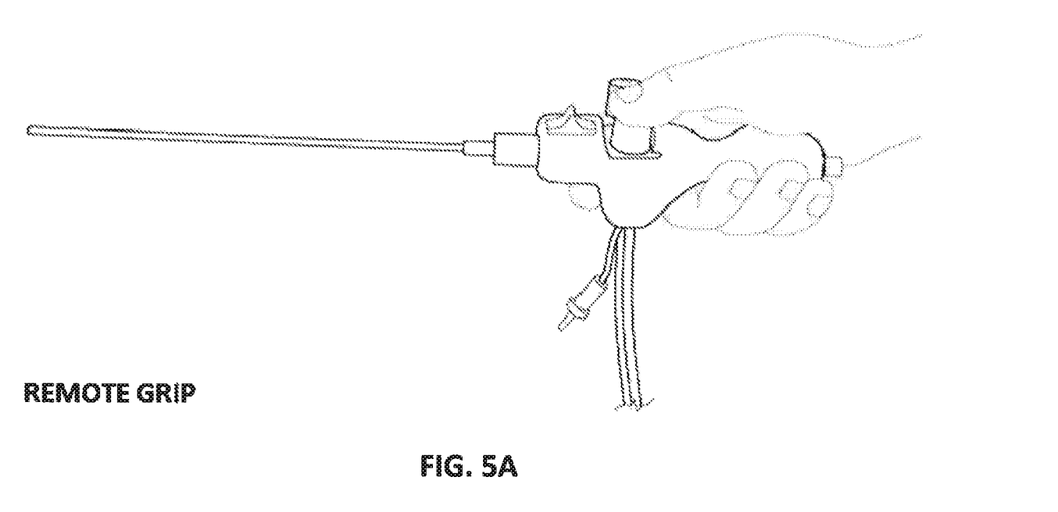
FIG. 5A presents a perspective view of the Remote Grip.
Figure 5B:
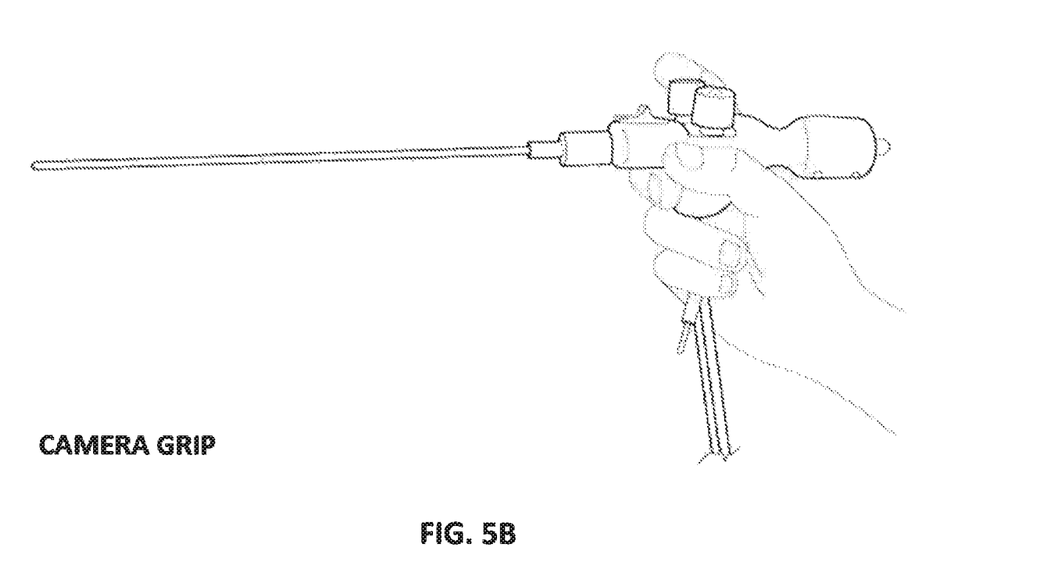
FIG. 5B presents a perspective view of a Camera Grip.
Figure 6:
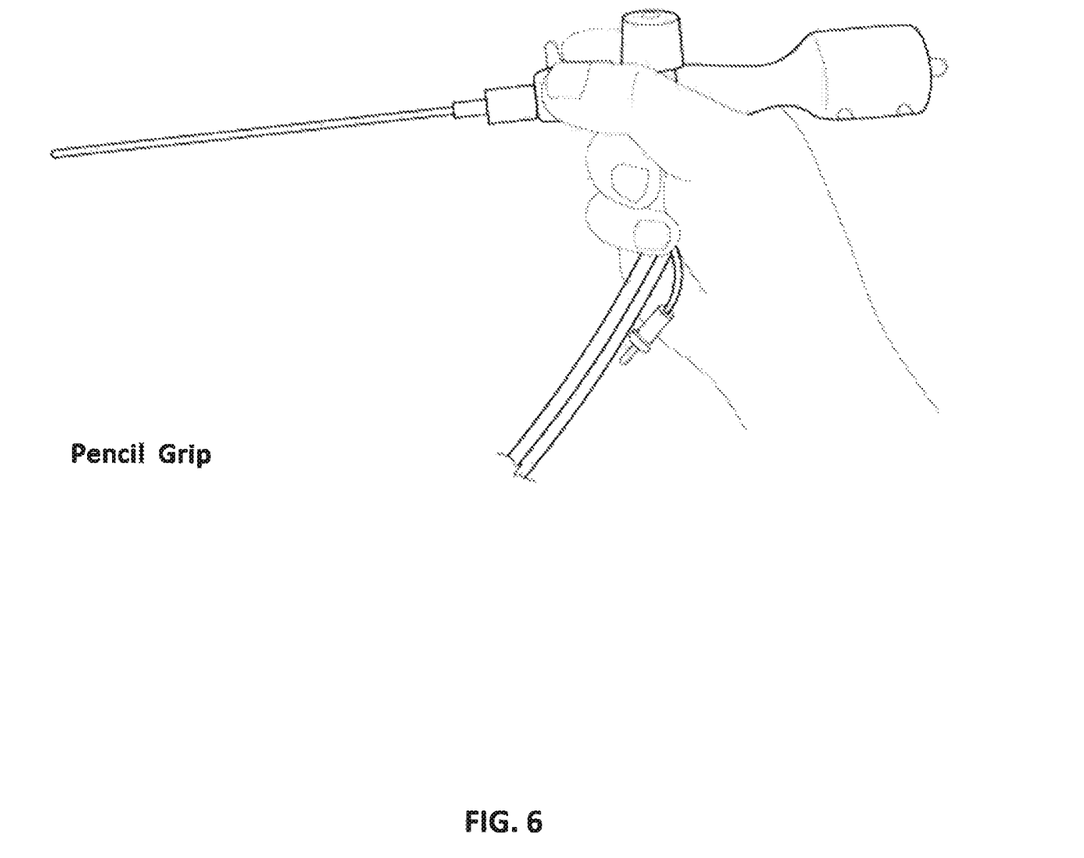
FIG. 6 presents a perspective view of the Pencil Grip.

An ergonomic laparoscopic device 100 is presented in various configurations in the illustrations of FIGS. 1 through 3. As shown therein, the laparoscopic device includes a main body 101 having a top, a bottom, and opposed first and second sides. The main body 101 includes a flared, first resting area 108, a second resting area 120 forward of the first resting area 108, and a downwardly depending weighted area 109, the purposes of which will be described hereinafter. The device 100 further includes a ballast or balancer element 104 connected to the rear of the main body 101 through a recessed or narrow portion 106 (also referred to herein as recessed hand purlicue area 106). The recessed hand purlicue area 106 has a reduced cross-sectional area as compared to the ballast 104 and main body 101.

In an embodiment, the ballast 104 has an elongated ellipsoid shape, although other configurations are also possible without departing from the broader aspects of the invention. As discussed below, the length of the ballast 104 may be selected to provide for optimal balancing of the laparoscopic device. In some embodiments, the length of the ballast 104 is variable or adjustable to provide proper balancing. The ballast 104 may be held in place by 4 screws attaching the bottom half to the top half, although other attachment means are also possible.

With further reference to FIGS. 1-3, the laparoscopic device 100 includes a shaft connector 122 that connects an elongated shaft 124 to the main body 101. The elongated shaft 124 is configured to receive a head 126 having a distal tip. As best shown in FIGS. 2 and 3, suction tubing 110 and irrigation tubing 112, as well as a cauterizing plug 118 are connected to the main body 101, preferably at the bottom/underside thereof (e.g., through the weighted area 109). A suction knob 114 and an irrigation knob 116 are located atop the main body 101 and are actuatable via an index finger and thumb of a user to control the suction and irrigation functions of the device 100.

With reference to FIGS. 4A-6, the recessed hand purlicue area 106 provides a resting area for the hand of the user, and the flared resting area 108 puts into communication the purlicue area 106 of the hand with the laparoscopic device 100, for better gripping and comfort. In particular, the recessed purlicue area 106 permits the hand to rest comfortably, while the flared resting area 108 helps draw the device 100 to the hand. Importantly, therefore, the laparoscopic device 100 is designed in such a way that it comfortably rests in the hand of the user.

Referring once again to FIG. 1, the main body 101 encompasses the hand holding area 130 which is used to balance the distal area 132 of the laparoscopic device 100. The laparoscopic device 100 pivots slightly downward about its fulcrum located near the tubing area (i.e., the area where the suction tubing 110 and irrigation tubing 112 connect to the main body 101), thereby allowing the weight of the tubing to pull down centrally, increasing stability in the hand. This is in contrast to most existing suction irrigators, which position the suction irrigation tubing at the rear of the device which causes the tip of the device to tilt upward. This upward action forces the person holding the device to grasp it tighter and counter balance it downwards, which may not seem like much effort, but after 30 minutes or so it can start putting a strain on the hand.

Importantly, and as perhaps best shown in FIGS. 2 and 3, the suction tubing 110, irrigation tubing 112, and cauterizing plug 118 are all adjoined, helping to provide a center of balance. The main body 101 and ballast 104 (i.e., the portion of the device denoted by reference numeral 130 in FIG. 1) balances the distal body 132 of the laparoscopic device 100 at its fulcrum point near the tubing area. As indicated above, the elongated ellipsoid shaped balancer 104 can be designed longer to properly balance longer elongated shafts 124.

Referring once again to FIG. 3, a side perspective view of the laparoscopic device 100 is illustrated showing how the device is in a slightly downward tilt. This downward tilt helps keep the fingers comfortably situated in the resting area 120 with little to no effort. The elongated ellipsoid shaped balancer 104 is configured to help balance the weight of the distal area 132 of FIG. 1. As the weight of the distal area 132 changes due to a longer or shorter elongated shaft 124, the elongated ellipsoid shaped balancer, i.e., ballast 124, is designed to counter balance the weight. The suction tubing 110, irrigation tubing 112 and cauterizing plug connector 122 are all situated about the fulcrum point 133 of FIG. 1. The fulcrum point 133 is an invisible vertical line where equilibrium of the laparoscopic device 100 is located. The suction knob 114, irrigation knob 116, and inner shaft controller 115 are all located along the fulcrum point 133. The area between the shaft connector 122 and the distal tip of the head 126 (e.g., peanut ablation head 126), produces a downward force to the main body 101.

In an embodiment, the suction knob 114 and suction tubing 112 are color coded to easily distinguish which knob works with which tubing. The cauterizing plug connector 118 is color coded different, such as, for example, the color red, to indicate that an electrical current will flow through it. The current path will follow a metal rod (not shown) located inside the elongated shaft 124 to a spatula tip, of FIG. 1.

The main body 101 defining the handle of the device 100 is preferably made of, but not limited to, polycarbonate materials which have excellent heat resistance properties that can be combined with flame retardant materials without significant material degradation. The polycarbonate material is also excellent in its light weight characteristics. The handle design does not have to be limited to suction/irrigation devices, but could be used on any laparoscopic instrument to improve ergonomics and accommodate a wider variety of grips.

While the above description provides examples of the embodiments, it will be appreciated that some features and/or functions of the described embodiments are susceptible to modification without departing from the spirit and principles of operation of the described embodiments. Accordingly, what has been described above has been intended to be illustrative of the invention and non-limiting and it will be understood by persons skilled in the art that other variants and modifications may be made without departing from the scope of the invention as defined in the claims appended hereto. The scope of the claims should not be limited by the preferred embodiments and examples, but should be given the broadest interpretation consistent with the description as a whole.

What is claimed is:

1. An ergonomic laparoscopic device, comprising:
a main body having a tubing area for the connection of tubing to the laparoscopic device, and a downwardly depending weighted portion defining a fulcrum of the laparoscopic device, the fulcrum defining an equilibrium point of the laparoscopic device;
an elongated shaft having a head having a distal tip, the elongated shaft extending forward from the main body;
a ballast extending rearward from the main body and being configured to counterbalance the weight of the elongated shaft; and
a recessed hand purlicue area intermediate the ballast and the main body;
wherein the ballast is elongated in shape;
wherein the main body, ballast, and hand purlicue area together define an hourglass shape; and
wherein the ballast and the downwardly depending weighted portion are integral and non-removable with respect to the main body.

2. The laparoscopic device of claim 1, wherein:
the main body includes a first flared resting area and a second resting area forward of the first flared resting area, the second resting area extending forwardly from the main body opposite the ballast in a direction parallel to an axis extending through the elongated shaft,
wherein the first flared resting area is configured to draw the laparoscopic device to a hand; and
wherein the second resting area is integral and non-removable with respect to the main body.

3. The laparoscopic device of claim 1, further comprising:
a suction knob and an irrigation knob located on a top side of the main body;
wherein the tubing includes a suction tube and an irrigation tube; and
wherein the suction tube and the irrigation tube are connected to an underside of the downwardly depending weighted portion, opposite the suction knob and the irrigation knob.

4. The laparoscopic device of claim 3, wherein:
the suction knob and the irrigation knob are actuatable with an index finger and thumb, and
wherein the suction knob and the irrigation knob are disposed along the fulcrum.

5. The laparoscopic device of claim 1, wherein the main body is formed from a polycarbonate material having heat resistant properties.

6. The laparoscopic device of claim 5, wherein:
the material is a flame-retardant material.

7. The laparoscopic device of claim 3, further comprising:
a cauterizing plug.

8. The laparoscopic device of claim 7, wherein:
the cauterizing plug, suction tubing, and irrigation tubing connect to the main body via the downwardly depending weighted portion of the main body and are situated about the fulcrum-on the main body.

9. The laparoscopic device of claim 1, wherein the head is a peanut ablation head.

10. The laparoscopic device of claim 1, wherein:
the suction knob, suction tubing, and cauterizing plug connector are colored; and
wherein the suction knob is a different color than the cauterizing plug connector.

11. An ergonomic laparoscopic device, comprising:
a main body having a top, a first side, a second side opposite the first side, and a bottom opposite the top;
an elongated ellipsoid shaped balancer along a proximal end of the laparoscopic device;
a recessed hand purlicue area intermediate the main body and the balancer;
a flared resting area extending forwardly from the main body opposite the balancer;
a suction knob, an irrigation knob, and an inner shaft controller located on the top of the main body;
a weighted portion extending downwardly from the main body;
a suction tube and an irrigation tube, the suction tube and the irrigation tube being connected to an underside of the weighted portion;
a cauterizing plug connector; and
an elongated shaft having a head having a distal tip, the elongated shaft extending from the main body opposite the balancer;
wherein the balancer and the weighted portion are integral and non-removable with respect to the main body.

12. The laparoscopic device of claim 11, wherein the main body comprises a polycarbonate material that comprises heat resistance properties.

13. The laparoscopic device of claim 11, wherein the main body comprises at least one flame retardant material.

14. The laparoscopic device of claim 11, wherein the balancer counter-balances the weight of the elongated shaft connected to the main body.

15. The laparoscopic device of claim 11, wherein the cauterizing plug connector is located on the underside of the weighted portion.

16. The laparoscopic device of claim 11, wherein the cauterizing plug connector is colored red.

17. The laparoscopic device of claim 3, wherein:
the suction knob and the irrigation knob are rotatable about a suction knob axis and an irrigation knob axis, respectively;
wherein the suction knob axis and the irrigation knob axis are non-parallel and are arranged in a V-shaped orientation.

18. An ergonomic laparoscopic device, comprising:
a main body having a top, a first side, a second side opposite the first side, and a bottom opposite the top;
an elongated ellipsoid shaped balancer along a proximal end of the laparoscopic device;

a recessed hand purlicue area intermediate the main body and the balancer;

a flared resting area extending forwardly from the main body opposite the balancer;

a suction knob, an irrigation knob, and an inner shaft controller located on the top of the main body;

a weighted portion extending downwardly from the main body;

a suction tube and an irrigation tube, the suction tube and the irrigation tube being connected to an underside of the weighted portion;

a cauterizing plug connector; and an elongated shaft having a head having a distal tip, the elongated shaft extending from the main body opposite the balancer;

wherein the suction knob and the irrigation knob are rotatable about a suction knob axis and an irrigation knob axis, respectively;

wherein the suction knob axis and the irrigation knob axis are non-parallel and are arranged in a V-shaped orientation.

19. The laparoscopic device of claim 11, wherein the suction knob and the irrigation knob are actuated with an index finger and a thumb.

* * * * *